(12) United States Patent
Takaishi et al.

(10) Patent No.: US 6,872,405 B2
(45) Date of Patent: Mar. 29, 2005

(54) QUICK-DISINTEGRATING TABLET IN BUCCAL CAVITY AND MANUFACTURING METHOD THEREOF

(75) Inventors: Yuuki Takaishi, Fujieda (JP); Takao Mizumoto, Shizuoka (JP); Yoshinori Masuda, Shizuoka (JP)

(73) Assignee: Yamanouchi Pharmaceutical Co., Ltd., Tokyo (JP)

( * ) Notice: Subject to any disclaimer, the term of this patent is extended or adjusted under 35 U.S.C. 154(b) by 13 days.

(21) Appl. No.: 10/142,081

(22) Filed: May 8, 2002

(65) Prior Publication Data

US 2003/0099701 A1 May 29, 2003

Related U.S. Application Data

(60) Provisional application No. 60/290,300, filed on May 10, 2001.

(51) Int. Cl.$^7$ ................................................. A61K 9/20

(52) U.S. Cl. ...................... 424/435; 424/439; 424/440; 424/441; 424/465

(58) Field of Search .............................. 424/435, 441, 424/465, 439, 440

(56) References Cited

U.S. PATENT DOCUMENTS

| | | |
|---|---|---|
| 5,534,555 A | 7/1996 | Meggelaars et al. |
| 5,576,014 A | 11/1996 | Mizumoto et al. |

(Continued)

FOREIGN PATENT DOCUMENTS

| | | |
|---|---|---|
| EP | 1 022 021 A1 | 7/2000 |
| EP | 1072256 | 1/2001 |

(Continued)

OTHER PUBLICATIONS

Copy of Search Report for Corresponding PCT application, PCT/JP02/04481.

*Primary Examiner*—James M. Spear
(74) *Attorney, Agent, or Firm*—Townsend and Townsend and Crew LLP

(57) ABSTRACT

The present invention relates to a quick-disintegrating tablet in the buccal cavity comprising a drug, a diluent, and a saccharide with a relatively lower melting point than the drug and the diluent, which is obtained by uniformly mixing the saccharide with a low melting point in the tablet so that a bridge will be formed between said drug and/or said diluent particles by the product of melting and then solidification of this saccharide with a low melting point. Moreover, the present invention relates to a method of manufacturing a quick-disintegrating tablet in the buccal cavity comprising a drug, a diluent and a saccharide with a relatively lower melting point than the drug and the diluent, which comprises (a) the process whereby tablet starting materials including a drug, a diluent, and a saccharide with a relatively lower melting point than the drug and the diluent are molded under the low pressure necessary for retaining the shape of a tablet, (b) the process whereby the molded product obtained in process (a) is heated to at least the temperature at which this saccharide with a low melting point will melt, and (c) the process whereby the molded product obtained in process (b) is cooled to at least the temperature at which the molten saccharide with a low melting point solidifies. The present invention presents a quick-disintegrating tablet in the buccal cavity that can be used for practical purposes in that it has almost the same properties as conventional oral pharmaceutical tablets, that is, it has sufficient tablet strength that it can be used with automatic unit dosing machines, and it is produced by conventional tableting machines, and a manufacturing method thereof. Moreover, the present invention presents a quick-disintegrating tablet in the buccal cavity which, in comparison to conventional quick-disintegrating tablets in the buccal cavity, has increased tablet strength and an improved friability without prolonging the disintegration time in the buccal cavity, and a manufacturing method thereof.

26 Claims, 1 Drawing Sheet

U.S. PATENT DOCUMENTS

| | | | |
|---|---|---|---|
| 5,837,285 | A | 11/1998 | Nakamichi et al. |
| 6,039,813 | A | 3/2000 | Pepper et al. |
| 6,083,438 | A | 7/2000 | Gonze et al. |
| 6,413,541 | B1 | 7/2002 | Shirai et al. |
| 2002/0071865 | A1 | 6/2002 | Kajiyama et al. |

FOREIGN PATENT DOCUMENTS

| | | |
|---|---|---|
| FR | 2 786 665 A | 6/2000 |
| GB | 1 084 864 A | 9/1967 |
| JP | A-H4-505918 | 10/1992 |
| JP | A-H5-170669 | 7/1993 |
| JP | A-H5-310558 | 11/1993 |
| JP | A-H9-309822 | 12/1997 |
| JP | 11-33084 | 2/1999 |
| JP | 11-35451 | 2/1999 |
| JP | A-H11-263723 | 9/1999 |
| JP | A-2001-58944 | 6/2001 |
| WO | WO 93/13758 | 7/1993 |
| WO | WO 95/20380 | 8/1995 |
| WO | WO 99/43306 | 9/1999 |
| WO | WO 00/04880 | 2/2000 |
| WO | WO 02/32403 A1 | 4/2002 |

QUICK-DISINTEGRATING TABLET IN BUCCAL CAVITY AND MANUFACTURING METHOD THEREOF

CROSS-REFERENCES TO RELATED APPLICATIONS

This application claims the benefit of U.S. provisional application No. 60/290,300 filed May 10, 2001.

BACKGROUND OF THE INVENTION

Field of the Invention

The present invention relates to a quick-disintegrating tablet in the buccal cavity compromising a drug, a diluent, and a saccharide with a relatively lower melting point than the drug and the diluent, which is obtained by uniformly mixing the saccharide with a low melting point in the tablet so that a bridge will be formed between the drug and/or diluent particles by the product of melting and then solidification of the saccharide with a low melting point. Moreover, the present invention relates to a method of manufacturing a quick-disintegrating tablet in the buccal cavity comprising a drug, a diluent, and a saccharide with a relatively lower melting point than the drug and the diluent, which consists of (a) the process whereby the tablet starting materials including a drug, a diluent, and a saccharide with a relatively lower melting point than the drug and the diluent are molded under the low pressure necessary for retaining the shape of a tablet, (b) the process whereby the molded product obtained in process (a) is heated to at least the temperature at which this saccharide with a low melting point will melt, and (c) the process whereby the molded product obtained in process (b) is cooled to at least the temperature at which the molten saccharide with a low melting point solidifies.

A variety of quick-disintegrating tablets in the buccal cavity that can be taken by the elderly and children without water have been developed in recent years. For instance, International Early Disclosure Pamphlet WO95/20380 (corresponds to U.S. Pat. No. 5,576,014, Japanese Patent No. 3122141) discloses a quick-disintegrating tablet in the buccal cavity obtained by granulation of a saccharide of low moldability with a saccharide of high moldability and then compression molding of this granulation product with a conventional tableting machine. This invention is characterized in that a saccharide of high moldability as the binder is sprayed and coated and/or granulated with a saccharide of low moldability, and discloses an invention with which humidification and drying can be performed when further tablet strength is necessary. Lactose, mannitol, glucose, sucrose, xylitol, and the like, are disclosed as saccharides of low moldability and maltose, maltitol, sorbitol, lactosucrose, and the like, are disclosed as saccharides of high moldability. Moreover, International Early Disclosure Pamphlet WO99/47124 discloses a quick-disintegrating tablet in the buccal cavity that is obtained by humidifying and drying a molded article after molding a granulation product, which is obtained by dissolving and/or suspending saccharide that can become amorphous in a pharmaceutically acceptable solvent and spraying and coating and/or granulating this on drug and/or saccharide, or after molding an amorphous saccharide, which is obtained by dissolving and/or suspending drug, saccharide and saccharide that can become amorphous in a pharmaceutically acceptable solvent and spray drying this solution and/or suspension. This invention is characterized in that molding is performed using a saccharide that can be converted to amorphous and then the molded article is humidified and dried in order to bind the tablet starting materials, such as drug and saccharide, and the like. That is, this invention has the characteristic of molding a drug, saccharide and saccharide that can be converted to amorphous, after which the saccharide capable of being converted to amorphous is converted to amorphous and then crystallized within the tablet by humidification and drying in order to improve tablet strength. This invention discloses mannitol, maltitol, erythritol, xylitol, and the like, as the saccharide (crystalline saccharide) and discloses lactose, sucrose, glucose, sorbitol, maltose, trehalose, lactitol, fructose, and the like, as the saccharide that can be converted to amorphous (saccharide that is crystallized by humidification and drying after conversion to amorphous). By means of these methods, it appears that tablet strength is sufficient for practical use and there are few major problems, but taking into consideration the fact that when compared to ordinary pharmaceutical tablets for oral use, tablet strength is somewhat low, particularly when an automatic unit-dose packaging machine is used, there is a need for further improvement of tablet strength and a reduction in the friability.

Moreover, Japanese Kokai Patent No. 11-35451 discloses a disintegrating tablet in the buccal cavity and a manufacturing method thereof, characterized in that drug effective component, saccharide, and substance with a low melting point, such as polyethylene glycol, and the like, are mixed, this mixture is tableted under low pressure, and the tablets that are obtained are heated to a temperature at which this substance with a low melting point will melt and then cooled. Nevertheless, there is no disclosure or indication of a specific means for increasing tablet strength and reducing the friability of a quick-disintegrating tablet in the buccal cavity comprising drug and saccharide, which is the main component of the pharmaceutical preparation staring materials. Furthermore, International Early Disclosure Pamphlet WO93/13758 (corresponds to Japanese Patent No. 2640570) discloses a method of manufacturing a tablet of increased strength comprising (a) the process whereby water-soluble binder capable of melting, at least 1 filler, and pharmaceutically active agent are combined and compressed into a tablet, (b) the process whereby the above-mentioned water-soluble binder capable of melting is melted in the above-mentioned tablet, and (c) the process whereby the above-mentioned water-soluble binder capable of melting is hardened. By means of this method, the melting point of the water-soluble binder capable of melting that is disclosed is generally 38~62° C. Therefore, there is room for further improvement of stability of the pharmaceutical preparation properties because there is a chance that tablet strength or disintegration time in the buccal cavity will change as a result of the binder re-melting over time when a pharmaceutical preparation that uses a binder with this melting point is stored in a place that is not properly air conditioned during the summer, and the like. Moreover, there is a tendency toward delayed dissolution in the buccal cavity and prolonged disintegration time in the buccal cavity with the polymers such as polyethylene glycol, and the like, and hydrophobic fillers, such as sucrose ester, and the like, that are disclosed as water-soluble binders capable of melting. Consequently, there is a demand from a medical standpoint for further development of new methods of manufacture that will increase tablet strength and reduce the friability of the tablet, or improve stability of pharmaceutical preparation properties, including disintegration time in the buccal cavity, and quick-disintegrating tablets in the buccal cavity manufactured by these methods.

Incidentally, U.S. Pat. No. 6,083,438 (corresponds to Japanese Kokai Patent No. 11-113525) discloses an invention relating to a filler for direct tableting, which is obtained by heating at a temperature at which two specific types of saccharides that are eutectic when heated, such erythritol and sorbitol, and the like, and then cooling and pulverizing the product that is obtained, and tablets made from this filler. This invention is a technology for producing the above-mentioned filler by the melt granulation method wherein a polyol that is eutectic with erythritol when heated is selected, its purpose being to present a tablet for conventional oral administration. Nevertheless, a quick-disintegrating tablet in the buccal cavity having a porous structure that is obtained by forming a bridge between particles by the product of melting and solidification of a saccharide with a low melting point only after low-pressure tableting is not disclosed or presented in this gazette.

DISCLOSURE THE INVENTION

Under these conditions, the inventors successfully completed the present invention upon discovering as a result of intense studies that, by means of prior art, (1) of saccharides with low moldability, that is, saccharides that function as a filler and do not function as a binder, there are saccharides that increase tablet strength by forming an interparticle bridge between a drug and/or a diluent particles by heat treatment so that the particles themselves firmly adhere to one another (for instance, erythritol), moreover, (2) of saccharides that will not convert to amorphous, that is, saccharides that function as filler and do not function as binder, there are saccharides that increase tablet strength by forming an interparticle bridge between the drug and/or the diluent particles by heat treatment so that the particles themselves firmly adhere to one another (for instance, erythritol and maltitol), and further, (3) a quick-disintegrating tablet in the buccal cavity with increased tablet strength and a reduced friability can be manufactured by, for instance, molding granulation product that has been obtained using two saccharides with different melting point temperatures, for instance, by spraying to coat and granulate "saccharide with a low melting point" as binder on "saccharide with a high melting point," then heating to melt only "saccharide with a low melting point," and forming an interparticle bridge between the drug and/or "saccharide with a high melting point" particles by the product of melting and then solidification of "saccharide with a low melting point" so that the particles themselves firmly adhere to one another.

That is, the present invention presents:

1. a quick-disintegrating tablet in the buccal cavity comprising a drug, a diluent, and a saccharide with a relatively lower melting point than the above-mentioned drug and above-mentioned diluent, which is obtained by uniformly mixing the saccharide with a low melting point in the tablet, and wherein a bridge is formed between the above-mentioned drug and/or above-mentioned diluent particles by the product of melting and then solidification of the saccharide with a low melting point, 2. the quick-disintegrating tablet in the buccal cavity of above-mentioned 1, wherein the saccharide with a low melting point is one whose melting point is at least 10° C. lower than that of the drug and diluent, 3. the quick-disintegrating tablet in the buccal cavity of above-mentioned 1 or 2, wherein the saccharide with a low melting point is one or two or more selected from the group consisting of xylitol, trehalose, maltose, sorbitol, erythritol, glucose, maltitol, mannitol, sucrose, and their hydrates, 4. the quick-disintegrating tablet in the buccal cavity in any one of above-mentioned 1 through 3, wherein the amount of saccharide with a low melting point is 0.5 to 25 w/w % in terms of the drug and/or the diluent, 5. the quick-disintegrating tablet in the buccal cavity in any one of above-mentioned 1 through 4, wherein a binder is further added, 6. the quick-disintegrating tablet in the buccal cavity in any one of above-mentioned 1 through 5, wherein the diluent is a saccharide with a relatively higher melting point than the saccharide with a low melting point in above-mentioned 1 through 4, 7. the quick-disintegrating tablet in the buccal cavity in above-mentioned 6, wherein the saccharide with a high melting point in above-mentioned 6 is one or two or more selected from the group consisting of xylitol, trehalose, maltose, sorbitol, erythritol, glucose, maltitol, mannitol, sucrose, lactose, and their hydrates, 8. the quick-disintegrating tablet in the buccal cavity in above-mentioned 7, wherein the saccharide with a high melting point in above-mentioned 7 is one or two or more selected from the group consisting of mannitol, sucrose, lactose, and their hydrates, 9. the quick-disintegrating tablet in the buccal cavity in any one of above-mentioned 1 through 8, wherein the saccharide with a low melting point in trehalose and/or erythritol and the saccharide with a high melting point is mannitol and/or lactose, 10. the quick-disintegrating tablet in the buccal cavity in above-mentioned 9, wherein the saccharide with a low melting point is erythritol and the saccharide with a high melting point is mannitol, 11. the quick-disintegrating tablet in the buccal cavity in above-mentioned 5, wherein the saccharide with high moldability and/or a water-soluble polymer serves as part of the binder, 12. the quick-disintegrating tablet in the buccal cavity in above-mentioned 11, wherein the binder is maltitol and/or copolyvidone, 13. the quick-disintegrating tablet in the buccal cavity in any one of above-mentioned 1 through 12, wherein porosity is 10 to 80%, 14. the quick-disintegrating tablet in the buccal cavity in above-mentioned 13, wherein porosity is 20 to 50%, 15. the quick-disintegrating tablet in the buccal cavity in any one of above-mentioned 1 through 14, where tablet hardness is 3 kp or higher and the friability is 1% or less, 16. the quick-disintegrating tablet in the buccal cavity in above-mentioned 15, where tablet hardness is 4 kp or higher and the friability is 0.8% or less, 17. the quick-disintegrating tablet in the buccal cavity in above-mentioned 16, wherein the friability is 0.5% or less, 18. the quick-disintegrating tablet in the buccal cavity in the above-mentioned 1 through 17, wherein the amount of drug added is at least the effective amount in terms of treatment and no more than 80 w/w % tablet weight, 19. a method of manufacturing a quick-disintegrating tablet in the buccal cavity comprising a drug, a diluent and a saccharide with a relatively lower melting point than the above-mentioned drug and above-mentioned diluent, which comprises: (a) the process whereby tablet starting materials including the drug, the diluent, and the saccharide with a relatively lower melting point than the above-mentioned drug and above-mentioned diluent are molded under the low pressure necessary for retaining the shape of a tablet, (b) the process whereby the molded product obtained by process (a) is heated to at least the temperature at which the saccharide with a low melting point will melt, and (c) the process whereby the molded product obtained by process (b) is cooled to at least the temperature at which the molten saccharide with a low melting point solidifies, 20. the method of manufacturing a quick-disintegrating tablet in the buccal cavity of above-mentioned 19, wherein by means of process (a) in above-mentioned 19, the drug, the diluent, and the saccharide with a relatively lower melting point than the above-mentioned drug and the above-mentioned diluent are physically mixed to obtain the tablet starting materials, 21. the method of manufacturing a quick-disintegrating tablet in the buccal cavity in above-mentioned 19, wherein by means of process (a) in above-mentioned 19, the saccharide with a low melting point is dissolved and/or suspended in a pharmaceutically acceptable solvent and sprayed as a binder for coating and/or granulation to obtain the tablet starting materials, 22. the method of manufacturing a quick-disintegrating tablet in the buccal cavity is above-mentioned 19, wherein by means of process (a) in above-mentioned 19, the saccharide with a low melting point is mixed with the drug and the diluent as particles and/or powder and granulation is performed using a binder solution to obtain the tablet starting materials, 23. the method of manufacturing a quick-disintegrating tablet in the buccal cavity in above-mentioned 19, wherein by means of process (a) in above-mentioned 19, the tablet starting materials are molded under a tableting pressure of 25 to 800 kg/punch, 24. the method of manufacturing a quick-disintegrating tablet in the buccal cavity in above-mentioned 19, wherein by means of process (b) in above-mentioned 19, heating is performed at a temperature between the melting point of the saccharide with a low melting point and the melting point of the drug and diluent, 25. the method of manufacturing a quick-disintegrating tablet and the buccal cavity in above-mentioned 19, which further comprises (d) the process whereby the molded product is humidified and dried, 26. the method of manufacturing a quick-disintegrating tablet in the buccal cavity in above-mentioned 25, wherein process (d) of above-mentioned 25 is between process (a) and process (b), or after process (c).

The quick-disintegrating tablet in the buccal cavity of the present invention is characterized in that it comprises a drug, a diluent, and a saccharide with a relatively lower melting point than the above-mentioned drug and above-mentioned diluent, or it comprises drug and saccharide with a relatively lower melting point than the above-mentioned drug, and saccharide with a relatively low melting point only melts and solidifies and a bridge is formed by this product of melting and solidification, particularly in that this tablet has a porous structure. Of the various quick-disintegrating tablets in the buccal cavity that have been developed, this characterization improves tablet strength and the friability when compared to conventional quick-disintegrating tablets in the buccal cavity while retaining porous structure, the quick-disintegrating tablet in the buccal cavity of the present invention has the superior effect of being able to improve tablet strength (3 kp or higher, preferably 4 kp or higher) and keep low (1% or less, preferably 0.8% or less, further preferably 0.5% or less) the friability of a tablet made mainly of the same type of saccharide while retaining a fast disintegration time in the buccal cavity (approximately less than 1 minute, preferably approximately less than 40 seconds, further preferably approximately less than 30 seconds).

The "quick-disintegrating tablet in the buccal cavity" used in the present invention means a tablet that is disintegrated in the buccal cavity in less than 1 minute (preferably less than approximately 40 seconds, further preferably less than approximately 30 seconds) essentially by saliva only without drinking water when the tablet is taken.

The "uniformly" in the present invention means the state where the saccharide with a low melting point is present uniformly dispersed as a whole in the tablet, that is, in a state where there is no maldistribution. FIG. 1 shows some of the embodiments, but the present invention is not limited to these embodiments.

The "formation of an interparticle bridge" in the present invention means the state where the drug and/or the diluent particles are made to adhere to one another by the product of melting and solidification of the saccharide with a relatively lower melting point than the drug and diluent.

The "shape of a tablet is retained" of the present invention means that there are essentially no "cracks" or "defects" made in a pharmaceutical tablet for oral use when handled as usual.

The "melting point" of the saccharide of the present invention means the temperature at which the saccharide with a low melting point used in the present invention begins to melt.

The "heating" in the present invention means bringing temperature of the saccharide with a low melting point used in the present invention to its melting point or higher.

The "cooling" in the present invention means bringing temperature of the saccharide with a low melting point used in the present invention to its melting point or lower for solidification.

The quick-disintegrating tablet in the buccal cavity and manufacturing method thereof of the present invention will now be described in detail:

There are no particular restrictions to the drug used in the present invention as long as it is an active component that is effective in terms of treatment or an active component that is effective in terms of prevention. Examples of the pharmaceutically active component are hypnotic sedatives, sleep-inducing agents, anti-anxiety drugs, anti-epilepsy drugs, antidepressants, anti-Parkinson's drugs, psychoneurotic drugs, central nervous system drugs, local anesthetics, skeletal muscle relaxants, autonomic nerve drugs, antipyretic analgesic anti-inflammatory agents, antispasmodics, anti-vertigo drugs, cardiotonics, drugs for arrhythmia, diuretics, hypotensives, vasoconstrictors, vasodilators, drugs for the circulatory system, drugs for hyperlipidemia, drugs to promote respiration, antitussives, expectorants, antitussive expectorants, bronchodilators, antidiarrheal agents, drugs for controlling intestinal function, drugs for peptic ulcer, stomachics, antacids, laxatives, cholagogues, gastrointestinal drugs, adrenocortical hormones, hormones, urogenital drugs, vitamins, hemostatics, drugs for liver disease, drugs used for gout, drugs used for diabetes, antihistamines, antibiotics, antibacterials, drugs used against malignant tumors, chemotherapeutic drugs, multisymptom cold medications, nutrition-enhancing health drugs, osteoporosis drugs, and the like. Examples of these drugs are anti-inflammatory, antipyretic antispasmodics or analgesics, such as indomethacin, diclofenac, diclofenac sodium, codeine, ibuprofen, phenylbutazone, oxygenbutazone, mepirizole, aspirin, idensamide, acetaminophen, aminopyrine, phenacetin, butyl scopolamine bromide, morphine, etomidoline, pentazocine, fenoprofen calcium, naproxen, celecoxib, vardecoxib, tramadole, and the like, antirheumatic drugs, such as etodolac, and the like, antituberculosis drugs, such as isoniazide, ethambutol chloride, and the like, drugs for the circulatory system, such as isosorbid nitrate, nitroglycerin, nifedipine, bardnidipine hydrochloride, nicardipine hydrochloride, dipyridamile, amrinone, indenolol hydrochloride, hydralazine hydrochloride, methyl dopa, furosemide, spironolactone, guanetidine nitrate, resperine, amosulalol hydrochloride, lisinoopril, methoprolol, pilocarbpine, tasosartan, and the like, psychoneurotic drugs, such as chlorpromazine hydrochloride, amitriptyline hydrochloride, nemonapride, haloperidole, moperone hydrochloride, perphenazine, diazepam, lorazepam, chlordiazepoxide, adinazolam, alprazolam, methylphenidate, milnasivran, peroxetin, risperidone, sodium valproate, and the like, antiemetics, such as methoclopramide, ramosetron hydrochloride, granisetron hydrochloride, ondansetron hydrochloride, azasetron hydrochloride, and the like antihistamines, such as chlorpheniramine maleate, diphenhydramine hydrochloride, and the like, vitamins, such as thiamine nitrate, tocopherol hydrochloride, sicotiamine, pyridoxal phosphate, cobamamide, ascorbic acid, nicotinamide, and the like, antigout drugs, such as allopurinol, colchicine, probenamide, and the like, anti-Parkinson's drugs, such as levo dopa, selegiline, and the like, hypnotic sedatives, such as amobarbital, bromwarelyl urea, midazolam, chloral hydrate, anti-malignant tumor drugs, such as fluorouracil, carmofur, aclarubicin hydrochloride, and the like, antiallergy drugs, such as busoidephedrine, terfenadine, and the like, antidepressants, such as phenyl propanolamine, ephedrins, and the like, drugs used to treat diabetes, such acethexamide, insulin, torbutamide, desmopressine, glibizide, and the like, diuretics, such as hydrochlorthiazide, polythiazide, triaterene, and the like, bronchodilators, such as aminophyllin, formoterol fumarate, theophylline, and the like, antitussives, such as codeine phosphate, noscapine, dimemorphan phosphate, dextromethorphan, and the like, antiarrythmia drugs, such as quinidine nitrate, digitoxin, propafenone hydrochloride, procainamide, and the like, surface anesthetics, such as aminoethyl benzoate, lidocaine, dibucaine hydrochloride, and the like, antiepilepsy drugs, such as phenytoin, etosuccimide, primidone, and the like, synthetic corticosteroids, such as hydrocortisone, prednisolone, triamcinolone, betamethasone, and the like, drugs for the digestive tract, such as famotidine, ranitidine hydrochloride, dimethisone, sucralfate, sulpiride, tepronone, praunotol, 5-aminosalicylic acid, sulfasalazine, omeprazole, lansoprazole, and the like, drugs for the central nervous system, such as indeloxazine, idebenone, thiapride hydrochloride, bifermerane hydrochloride, calcium homopanthothenate, and the like, agents for treatment of hyperlipidemia, such as pravastatin sodium, sinvastatin, lovastatin, prevastatin, atorvastatin, and the like, antibiotics, such as ampicillin phthalizyl hydrochloride, cefotetan, josamycin, and the like, BPH therapeutic agents, such as tamsulosin, doxazocin mesilate, terazosine hydrochloride, and the like, anti-asthma agents, such as pranrucast, zafirlukast, albuterol, ambrozole, budesonide, leverbuterol, and the like, prostaglandin I derivative agents for improving peripheral circulation, such as velaprost sodium, and the like, antithrombotics, hypotensives, agents for treatment of heart failure, agents for treatment of various complications of diabetes, agents for treatment of peptic ulcer, agents for treatment of skin ulcers, agents for treatment of hyperlipidemia, anti-asthma agents, and the like. The drug can be used in free form or as any salt that is pharmaceutically acceptable. Moreover, 1 or a combination of 2 or more drugs can be used.

There are no special restrictions to the amount of this drug as long as it is the amount that is normally used for treatment, but it is at least the effective amount in terms of treatment and no more than 80 w/w % tablet weight, preferably at least the effective amount in terms of treatment and no more than 70 w/w % tablet weight. By means of the present invention, sufficient tablet strength is obtained while retaining a porous structure and therefore, it is possible to increase the amount of drug that is added in terms of tablet weight. Moreover, when particle diameter of the drug is large, it becomes the source of a gritty feeling when it is disintegrated in the buccal cavity and therefore, a mean particle diameter of 250 $\mu$m or smaller is preferred. When mean particle diameter of the drug is 250 $\mu$m or larger, it is used usually after being pulverized to a size of a mean particle diameter of approximately 1 to 200 $\mu$m, preferably after being pulverized to a size of a mean particle diameter of approximately 5 to 100 $\mu$m, further preferably after being pulverized to a size of a mean particle diameter of approximately 5 to approximately 30 $\mu$m, using an appropriate pulverizing device, such as a hammer mill, sample mill, jet mill, and the like.

Moreover, when the drug of the present invention is a drug with a bitter taste and/or poor fluidity, it can be mixed with a carrier that is pharmaceutically acceptable and that reduces the bitter taste of the drug, or that can improve the fluidity of the drug. Polymer substances, including water-insoluble polymers, gastrosoluble polymers, enterosoluble polymers, wax-like substances, and the like, are examples of this carrier. Examples of water-insoluble polymers are water-insoluble cellulose ether, such as ethyl cellulose, Aquacoat (brand name, Asahi Kasei), and the like, water-insoluble acrylic acid copolymers, such as ethyl acrylate-methyl methacrylate-trimethyl ammonium chloride ethyl methacrylate copolymer (for instance, brand name: Eudragit RS, Eudragit RS30D, Röhm), methyl methacrylate-ethyl acrylate copolymer (for instance, brand name: Eudragit NE30D, Röhm), and the like, and the like, Examples of gastrosoluble polymers are gastrosoluble polyvinyl derivatives, such as polyvinyl acetal diethyl aminoacetate, and the like, gastrosoluble acrylic acid copolymers such as methyl methacrylate-butyl methacrylate-dimethylaminoethyl methacrylate copolymer (for instance, brand name: Eudragit E, Röhm), and the like, and the like. Examples of enterosoluble polymers are enterosoluble cellulose derivatives, such as hydroxypropylmethyl cellulose acetate succinate, hydroxypropyl methyl cellulose phthalate, hydroxymethyl ethyl cellulose phthalate, carboxymethyl ethyl cellulose, and the like, enterosoluble acrylic acid copolymers, such as methacrylic acid copolymer L (for instance, brand name: Eudragit L, Röhm), methacrylic acid copolymer LD (for instance, brand name: Eudragit L30D-55, Röhm), and the like, and the like. Examples of wax-like substances are solid oils and fats, such as hydrogenated castor oil, hydrogenated coconut oil, tallow, and the like, higher fatty acids, such as stearic acid, lauric acid, myristic acid, palmitic acid, and the like, higher alcohols, such as cetyl alcohol, stearyl alcohol, and the like. Of these, pH-independent water-insoluble polymer is preferred, water-insoluble cellulose ether or water-insoluble acrylic acid copolymer is further preferred, and ethyl cellulose (ideally Aquacoat (brand name: aqueous ethyl cellulose dispersion) or ethyl acrylate.methyl methacrylate.chlorinated trimethylammoniummethyl methacrylate copolymer (ideally Eudragit RS30D (brand name)) is particularly preferred. Plasticizer can also be added as needed to the carrier of the present invention. Examples of this plasticizer are triacetin, triethyl citrate, dibutyl sebacate, acetylated monoglyceride, Eudragit NE30D (brand name, Röhm), and the like. Moreover, fluidity of drugs that do not have a bitter taste or an unpleasant odor can be improved, and in addition to the above-mentioned polymer substances, such as water-insoluble polymers, gastrosoluble polymers, enterosoluble polymer, and the like, or their wax-like substances, and the like, water-soluble polymers, saccharides, and the like, can be used as carrier in this case. Examples of this carrier are water-soluble polymers, such as hydroxypropyl cellulose, hydroxypropyl methyl cellulose, polyvinyl pyrrolidone, copolyvidone, polyvinyl alcohol, and the like. The amount of carrier used here can be adjusted as needed based on how bitter tasting or how fluid the drug is, but it is usually 5 to 300 w/w %, preferably 10 to 100 w/w %, further preferably 20 to 100 w/w %, per drug. When the drug is famotidine, it is 20 to 100 w/w %, preferably 30 to 50 w/w %, per famotidine. Moreover, when drug that should be sustained-release is used in the present invention, it is preferred that the appropriate sustained-release treatment (for instance, refer to Japanese Kokai Patent No. Hei 7-72129) be performed by conventional methods so that particles with which release of the drug is controlled are obtained. Furthermore, since the tablet of the present invention is disintegrated and dissolved in the buccal cavity, the drug can also be absorbed in the buccal cavity if it is a drug that is absorbed by the mucous membrane of the buccal cavity.

There are no special restrictions to the diluent used in the present invention as long as it has a relatively higher melting point than the saccharide that forms the product of melting and solidification used in the present invention and it quickly disintegrates in the buccal cavity when this diluent is molded into a tablet. Saccharides with a relatively higher melting point than the saccharide used in the present invention, inorganic substances such as anhydrous calcium phosphate, precipitated calcium carbonate, calcium silicate, and the like, crystalline cellulose (for instance, brand-name: Avicel, Asahi Kasei), and the like, are given as examples. Saccharides with a high melting point are preferred. Saccharides with a melting point temperature difference of at least 10° C., preferably saccharides with a melting point temperature differences of at least 20° C., from the saccharide with a low melting point used in the present invention are the saccharide with a high melting point used in the present invention. Selection of saccharides with a larger melting point difference is preferred taking into consideration the difference between that design temperature of the heating device and the temperature of the tablet, which is the subject of heating.

The amount of diluent used in the present invention is adjusted as needed in accordance with the dose of the drug and/or size of the tablet, and there are no special restrictions as long as the "saccharide with a low melting point" used in the present invention forms a bridge between the drug and/or diluent particles so that the shape of a tablet made from drug and diluent can be retained. This amount added is adjusted as needed so that a tablet of the desired size is obtained by increasing the amount added when the dose of drug is small, reducing the amount added when the dose of drug is large, and the like, but it is usually 20 to 1,000 mg, preferably 50 to 500 mg, further preferably 100 to 400 mg, per 1 tablet. Moreover, it is 10 to 99.5 w/w %, preferably 20 to 95 w/w %, per tablet weight. The mixture ratio of diluent used in the present invention is preferably 99.5:0.5 to 75:25, further preferably 98:2 to 80:20, to the "saccharide with a low melting point" used in the present invention.

There are no special restrictions to the saccharide with a low melting point used in the present invention (also referred to hereafter as "saccharide") as long as it is pharmaceutically acceptable and has a relatively lower melting point than the drug and diluent used in the present invention, and it maintains the shape of the tablets by melting and solidifying. However, saccharides with a melting point of approximately 80 to approximately 180° C. are preferred and saccharide with a melting point of approximately 90 to 150° C. are further preferred. Glucose (monohydrate, melting point of 83° C.), xylitol (melting point of 93° C.), trehalose (dihydrate, melting point of 97° C.), sorbitol (hydrate, melting point of less than 100° C.), maltose (melting point of 102° C.), sorbitol (melting point of 110° C.), erythritol (melting point of 122° C.), glucose (melting point of 146° C.), maltitol (melting point of 150° C.), mannitol (melting point of 166° C.), sucrose (melting point of approximately 170° C.), are examples of these saccharides. One or two or more saccharides selected from the group consisting of glucose, xylitol, trehalose, sorbitol, maltose, erythritol, maltitol, mannitol, sucrose, and their hydrates are used as this saccharide. One or two or more saccharides selected from the group consisting of glucose, xylitol, trehalose, sorbitol, maltose, erythritol, maltitol, and their hydrates are preferred. Trehalose, maltose, erythritol, or maltitol, which are easy to handle because these saccharides themselves are hardly moisture absorbing, are ideal, and trehalose and/or erythritol are particularly ideal. The saccharide of the present invention can be selected as needed taking into consideration chemical properties of the drug that is used, that is, stability of the drug with regard to temperature. Moreover, one or a combination of two or more of these saccharides can be used. In addition, it is also possible to use these saccharides as hydrates. When there is a difference between the melting points of the hydrate and the anhydrous form of the saccharide, heating temperature should be selected accordingly.

The amount of saccharide ("saccharide with a low melting point") used in the present invention is adjusted as needed in accordance with the dose of the drug and/or size of the tablet, and there are no special restrictions as long as a bridge is formed between the drug and/or diluent particles by the product of melting and solidification of the saccharide with a low melting point so that the shape of a tablet made from drug and diluent can be retained. This amount added is adjusted as needed so that a tablet of the desired size is obtained by increasing the amount of diluent used in the present invention when the dose of drug is small, reducing the amount of diluent used in the present invention when the dose of drug is large, and the like. Consequently, the amount of "saccharide with a low melting point" used in the present invention is usually 0.5 to 25 w/w %, preferably 2 to 20 w/w %, further preferably 5 to 10 w/w %, in terms of the weight of the drug and/or diluent used in the present invention, or 2 to 20 w/w % of the total pharmaceutical preparation.

Xylitol (melting point of 93° C.), trehalose (dihydrate, melting point of 97° C.), sorbitol (hydrate, melting point of less than 100° C.), maltose (melting point of 102° C.), sorbitol (melting point of 110° C.), erythritol (melting point of 122° C.), glucose (melting point of 146° C.), maltitol (melting point of 150° C.), mannitol (melting point of 166° C.), sucrose (melting point of approximately 170° C.), and lactose (melting point of 202° C.), and the like, are given as the saccharide with a relatively "higher melting point" than the saccharide with a low melting point used in the present invention. One or two or more saccharides selected from the group consisting of xylitol, trehalose, sorbitol hydrate, maltose, sorbitol, erythritol, glucose, maltitol, mannitol, sucrose, lactose and their hydrates are examples of this saccharide. When described in specific terms, xylitol, trehalose, sorbitol, erythritol, glucose, maltitol, mannitol, sucrose, lactose, and their hydrates can be used as the "saccharide with a high melting point" when glucose (monohydrate, melting point of 83° C.) is used as the "saccharide with a low melting point" used in the present invention. Moreover, sorbitol, erythritol, glucose, maltitol, mannitol, sucrose, lactose, and their hydrates can be used as the "saccharide with a high melting point" when xylitol (melting point of 93° C.) or trehalose (dihydrate, 97° C.) is used as the "saccharide with a low melting point" used in the present invention. Glucose, maltitol, mannitol, sucrose or lactose can be used as the "saccharide with a high melting point" when erythritol (melting point of 122° C.) is used as the "saccharide with a low melting point" used in the present invention. Furthermore, mannitol, sucrose and lactose can be used as the "saccharide with a high melting point" when maltitol (melting point of 150° C.) is used as the "saccharide with a low melting point" in the present invention. In addition, lactose can be used as the "saccharide with a high melting point" when sucrose (melting point of approximately 170° C.) is used as the "saccharide with a low melting point" in the present invention. The "saccharide with a high melting point" should be selected as described, as necessary in accordance with the type of saccharide used in the present invention. When selecting the saccharides so that there is a greater difference between their melting points, the "saccharide with a high melting point" is preferably one or two or more saccharides selected from the group consisting of glucose, maltitol, mannitol, sucrose and lactose, and further preferably mannitol, sucrose, and lactose. These are used in the appropriate amounts of one or a mixture of two or more as needed. If the difference in the melting point of the "saccharide with a high melting point" is small, there is a chance that the "saccharide with a low melting point" used in the present invention and the "saccharide with a high melting point" will melt and solidify together in the tablet and the saccharides contained in the tablet will form an interparticle bridge, resulting in the tablet strength increasing beyond what is necessary so that it will not quickly disintegrate in the buccal cavity. Consequently, selection of saccharides with a larger melting point temperature difference is preferred in terms of manufacturing a quick-disintegrating tablet in the buccal cavity. The melting point difference is preferably 10° C. or higher, further preferably 20° C. or higher.

There are no special restrictions to the binder as long as constant particle strength is obtained such that a picking or sticking phenomenon is not observed during tableting and moldability is improved when drug, diluent, and "saccharide with a low melting point", and further, other pharmaceutical fillers as needed, are granulated. "Saccharide with high moldability" or water-soluble polymer are given as examples of this binder. The "saccharide with high moldability" here means one that shows a tablet hardness of 2 kp or more when 150 mg saccharide are tableted under a tableting pressure of 10 to 50 kg/cm$^2$ using a punch with a diameter of 8 mm (referred to WO 95/20380 (corresponding U.S. Pat. No. 5,576,014, Japanese Patent No. 3122141)). Maltose, maltitol, sorbitol, and the like, are given as this saccharide. Maltitol that is crystalline even with heating and melting is preferred. Hydroxypropylcellulose, hydroxypropylmethylcellulose, polyvinyl pyrrolidone, copolyvidone, polyvinyl alcohol, and the like, are examples of water-soluble polymers. Taking into consideration the environment in which the starting materials and pharmaceutical preparation will be stored, hydroxypropylcellulose, hydroxypropylmethylcellulose, and copolyvidone with low moisture-absorbing capability are further preferred, and copolyvidone is ideal.

There are no special restrictions to the amount of "saccharide with high moldability" or water-soluble polymer added to the "saccharide with a low melting point" as long as it is the amount with which constant particle strength is obtained such that a picking or sticking phenomenon is not observed during tableting and moldability is improved when drug, diluent, and "saccharide with a low melting point", and further, pharmaceutical fillers other than binder as needed, are granulated. This amount is usually 0.5 to 20 w/w %. The amount of "saccharide with high moldability" is preferably 2 to 20 w/w %, further preferably 2 to 10 w/w %. The amount of water-soluble polymer is preferably 0.5 to 5 w/w %, further preferably 0.5 to 3 w/w %.

It is preferred that when combining "saccharide with a low melting point" of the present invention, "saccharide with a high melting point," and binder, erythritol is selected as the "saccharide with a low melting point," lactose and/or mannitol are selected as the "saccharide with a high melting point," and maltitol is selected as the binder ("saccharide with high moldability"), or erythritol is selected as the "saccharide with a low melting point" of the present invention, lactose and/or mannitol are selected as the "saccharide with a high melting point," and further, copolyvidone is selected as the binder ("water-soluble polymer").

There are no special restrictions to the pharmaceutical fillers other than diluent and binder used in the present invention as long as they are a variety of fillers that are pharmaceutically acceptable and used as additives. Disintegrators, sour flavoring, foaming agents, artificial sweeteners, fragrances, lubricants, coloration agents, stabilizers, and the like, are given as examples of these pharmaceutical fillers. One or a combination of two or more of these pharmaceutical fillers are used.

Corn starch, starch, carmellose calcium, carmellose sodium, polyvinyl alcohol, and the like, are examples of disintegrators. Examples of sour flavoring are citric acid, tartaric acid, malic acid, and the like. Examples of foaming agents are sodium bicarbonate, and the like. Examples of artificial sweeteners are saccharine sodium, glycyrrhizinate dipotassium, aspartame, stevia, sormatin, and the like. Examples of fragrances are lemon, lemon-lime, orange, menthol, and the like. Examples of lubricants are magnesium stearate, calcium stearate, sucrose fatty acid ester, polyethylene glycol, talc, stearic acid, and the like. Examples of coloration agents are food coloring, such as yellow food dye No. 5, red food dye No. 2, blue food dye No. 2, and the like; food lake coloring; red ferric oxide, and the like. Stabilizers are selected by drug after performing various tests. One or a combination of two or more of these additives can be added in an appropriate amount as needed. There are no special restrictions to the amount of pharmaceutical filler added as long as it is within the range normally used pharmaceutically by persons in the trade.

The processes, particularly the manufacturing conditions, and the like, involved in the method of manufacturing the quick-disintegrating tablet in the buccal cavity of the present invention will now be described in detail:

The method of manufacturing the quick-disintegrating tablet in the buccal cavity of the present invention consists of (a) the process whereby tablet starting materials including drug, diluent, and "saccharide with a relatively lower melting point" than the drug and diluent are molded under the low pressure necessary for retaining the shape of a tablet, (b) the process whereby the molded product obtained in process (a) is heated to at least the temperature at which this saccharide with a low melting point will melt, and (c) the process whereby the molded product obtained in process (b) is cooled to at least the temperature at which the molten saccharide with a low melting point will solidify.

Process (a): Molding Process

There are no special restrictions to the "tablet starting materials" of the present invention as long as the drug, diluent, and saccharide with a relatively lower melting point than the drug and diluent are in a state where they are uniformly dispersed pharmaceutically. These "tablet starting materials" can be prepared using physical mixing, spray drying, or a variety of granulation methods, such as fluid bed granulation, agitation granulation, tumbling granulation, and the like. Of these, fluid bed granulation is preferred in terms of productivity. By means of fluid bed granulation, for instance, the "tablet starting materials" are prepared by spraying a solution of the "saccharide with a low melting point" used in the present invention as the binder dissolved and/or suspended in a pharmaceutically acceptable solvent on the pharmaceutical diluent to coat and/or granulate. Moreover, the method of preparing "tablet starting materials" is given whereby "saccharide with a low melting point" is mixed with drug and/or diluent as particles and/or powder and granulated using a solution of "saccharide with high moldability" or water-soluble polymer. The drug is added in this case by, for instance, a process whereby "tablet starting materials" are prepared by uniformly mixing with granulation product containing the "saccharide with a low melting point" used in the present invention pharmaceutically, a process whereby "tablet starting materials" are prepared by spraying a solution of "saccharide with a low melting point" used in the present invention as the binder dissolved and/or suspended in a pharmaceutically acceptable solvent onto a mixture of drug and diluent to coat and/or granulate, and the like. Moreover, the method of preparing "tablet starting materials" is given whereby "saccharide with a low melting point" is mixed with drug and diluent as particles and/or powder and granulated using a solution of "saccharide with high moldability" or water-soluble polymer. Furthermore, the drug can be used as drug particles with improved fluidity or as particles whose bitter taste has been masked prepared by spray drying by the method in International Early Disclosure Pamphlet WO02/02083A1 (U.S. patent application Ser. No. 90/896,820; priority claim U.S. Provisional Patent Application Ser. No. 60/215,292).

The "molding" in the present invention can be performed by conventional methods, and there are no special restrictions as long as it is a method whereby the shape of a tablet is retained under the lower limit of pressure necessary to retain the shape of a tablet or higher. This "molding" can be performed using a conventional tableting machine, such as a single tableting machine or a rotary tableting machine, and the like, after mixing lubricant, and the like, with the above-mentioned "tablet starting materials." Tableting pressure in this case is usually 25~800 kg/punch, preferably 50~500 kg/punch, further preferably 50~300 kg/punch.

Process (b): Heating Process

The "heating" in the present invention is performed by conventional methods, and there are no special restrictions as long as it is a method whereby the molded product obtained by process (a) can be brought to a temperature that is at least the melting point of the "saccharide with a low melting point" used in the present invention. Moreover, heating whereby part of the saccharide used in the present invention is melted and fused is also included in the present invention. Said "heating" process can be performed, for instance, using a ventilation oven. Temperature conditions are selected as needed depending on the type of "saccharide with a low melting point" used in the present invention, and there usually are no particular restrictions as long as it is the melting point of the "saccharide with a low melting point" used in the present invention or higher and the melting point of the diluent or lower. When a "saccharide with a low melting point" used in the present invention is used, it is approximately 80 to approximately 180° C., preferably approximately 90 to approximately 150° C. Time conditions are selected as needed depending on the type of saccharide that is used, the desired tablet strength, disintegration performance in the buccal cavity, and the like, but it is usually 0.5 to 120 minutes, preferably 1 to 60 minutes, further preferably 2 to 30 minutes. Moreover, the "heating" and "cooling" process can also be performed after the "humidification" and "drying" processes that are described later.

Process (b): Cooling Process

The "cooling" in the present invention is performed by conventional methods, and there are no particular restrictions as long as it is a method whereby the saccharide with a low melting point used in the present invention solidifies after melting. Said "cooling" can be performed by, for instance, being set aside at room temperature or being stored in a low-temperature atmosphere, such as a refrigerator, and the like.

The humidification and drying process described below should be used when the saccharide with a low melting used in the present invention that has melted and solidified via the cooling process becomes amorphous and there is a reduction in tablet strength with absorption of moisture, that is, when glucose, sorbitol, maltose, or trehalose is used as the saccharide used in the present invention. It is possible to realize a stable tablet by using a process of humidification and drying in order to crystallize a saccharide that has become amorphous with heating. Moreover, the method whereby the state of conversion to amorphous can be retained with stability, for instance, the method of obtaining a stable pharmaceutical preparation by sealing inside an appropriate packaging material made from non-moisture permeable material, can also be used.

There are no particular restrictions to the "humidification" in the present invention as long as it is a method whereby the saccharide used in the present invention is crystallized after being converted to amorphous when conducted in combination with a drying process, which is the process following the heating process. This "humidification" method is determined from the apparent critical relative humidity of the drug, saccharide with a low melting point used in the present invention, and diluent used in the present invention. However, humidification is usually performed to the apparent critical relative humidity of this mixture or higher. For instance, humidity is 30 to 100% RH, preferably 50 to 90% RH. Temperature at this process is 15 to 50° C., preferably 20 to 40° C. Treatment time is 1 to 36 hours, preferably 12 to 24 hours.

There are no special restrictions to the "drying" in the present invention as long as it is a process by means of which the water content that has been absorbed with humidification is removed. Said "drying" is usually performed at 10 to 100° C., preferably 20 to 60° C., particularly 25 to 40° C. Treatment time is 0.5 to 5 hours, preferably 1 to 3 hours.

The quick-disintegrating tablet in the buccal cavity of the present invention obtained in this way has a porous structure. The porous structure here means that porosity is usually approximately 20 to approximately 80%, preferably approximately 20 to approximately 50%, further preferably approximately 30 to approximately 50%. By forming a bridge with the product of melting and solidification of the saccharide, it is possible to retain a porous structure and to retain the ability to quickly disintegrate in the buccal cavity, as well as to realize tablet strength and a friability capable of withstanding automatic unit dosing machines.

BRIEF DESCRIPTION OF THE DRAWINGS

FIG. 1-(A) is a schematic drawing showing the state before heat treatment when a "saccharide with a low melting point" (saccharide of a low melting point) is uniformly mixed in the tablet together with diluent, for instance "saccharide with a high melting point" (saccharide of a high melting point), and the like.

FIG. 1-(B) is a schematic drawing showing the state after heating. It appears that the "saccharide with a low melting point" (saccharide of a low melting point) of the present invention that has melted/solidified bonds between the particles of diluent, for instance, "saccharide with a high melting point" (saccharide of a high melting point), and the like, and as a result, improves physical strength. When this state is adopted by the entire tablet, it is manifested as improvement of tablet strength. The uniformly mixed here means that even when in a state where each component is present as particles and is not present uniformly dispersed, as a whole, the tablet is in a state where each component is present uniformly dispersed when observed on the particle level.

DESCRIPTION OF THE PREFERRED EMBODIMENTS

Figure 1:
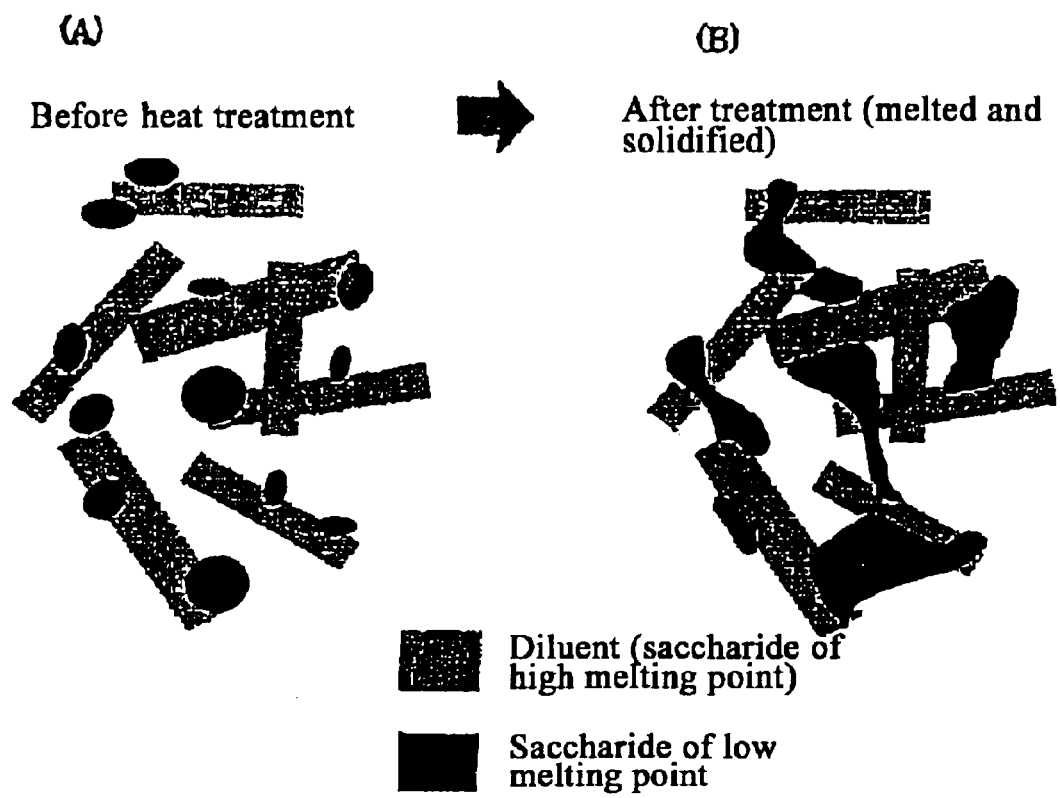
FIG. 1 is a schematic drawing showing the state of the saccharide before and after heat treatment of the tablets of the present invention, but the present invention is not limited to these drawings.

The present invention will now be explained in further detail while referring to examples, but the present invention is not limited to these examples. Furthermore, tablet strength, the friability, and the disintegration time in the buccal cavity are evaluated in the following Examples of the present invention, but because it appears that addition of drug has little effect on these evaluation items, the examples also include the results obtained from those tablets that do not contain drug.

Evaluation Methods

The methods for evaluating the quick disintegrating tablet in buccal cavity of the present invention are described below:

[Hardness tests] Determinations were performed using a Schleuniger tablet hardness tester (Schleuniger Co., Ltd.). The tests are performed with 5 tablets and the mean value is shown. Tablet hardness is represented by the force needed to crush the tablet (units kp). A larger number indicates a stronger tablet.

[Friability] Determinations were performed using an abrasion tester (model PTFR-A, Pharma Test Co.) The friability is found using 6 g tablets. It is represented by the percentage weight loss of a tablet after 100 rounds at a turning speed of 25 rpm. A smaller value indicates a stronger tablet surface.

[Disintegration in buccal cavity tests] Healthy adult males place the tablet of the present invention inside their buccal cavity without having any water inside their mouth and the time until the tablet is completely disintegrated and dissolved by saliva only is determined.

[Porosity] Porosity of the tablets was calculated from the following formula (I) and is the mean of five tablets.

$$\text{Porosity} = \frac{V - (W/\rho)}{V} \times 100 \quad \text{Fromula (I)}$$

($V$: tablet volume, $W$: tablet weight, $\rho$: specific gravity of powder making up tablet)

EXPERIMENT 1

Confirmation of Melting by Heating of Saccharide and Changes in its Crystal Form (Method)

After thoroughly crushing trehalose (Hayashibara Co., Ltd.), maltose (brand name Sunmalt-S, Hayashibara Co., Ltd), sorbitol, sucrose, mannitol (Towa kasei Co., Ltd.), erythritol (Hayashibara Co., Ltd.), xylitol (Towa Kasei Co., Ltd) as the saccharides with a mortar and punch, they were transferred to a glass dish and heat treated for 5 minutes at 140° C. using a program oven (model No. MOV-112P, Sanyo).

Melting of the saccharide was visually confirmed. After cooling the molten saccharide to room temperature, it was crushed again using a mortar and punch and determinations were performed with a differential scanning calorimeter (DSC hereafter) and crystal form was evaluated.

The maltose was further humidified over night under conditions of 25° C. and 75% RH using a thermostatic vessel at constant humidity (Tabaiespec Co., Ltd., PR-35C) and DSC determination was performed. A physical mixture of mannitol/maltose (9/1) and mannitol/trehalose (9/1) was further prepared and DSC determination was performed before heat treatment, after heat treatment and when humidification was performed after heat treatment to evaluate crystal form.

(Results)

Melting of the trehalose, maltose, sorbitol, xylitol, and erythritol by heating was confirmed. On the other hand, melting of sucrose and mannitol was not confirmed. Of the saccharides that had melted, the endothermic peak derived from crystals of trehalose and maltose disappeared, confirming conversion to amorphous. Moreover, recrystallization of saccharide that had converted to amorphous as a result of humidification amorphous saccharide was also confirmed. In contrast to this, crystallization of xylitol and erythritol was confirmed because the same endothermic peak as before heating was present. Only the peak of the "saccharide with a low melting point" used in the present invention disappeared, confirming conversion to amorphous, with each physical mixture of mannitol/maltose and mannitol/trehalose. Moreover, the peak of a "saccharide with a low melting point" used in the present invention appeared after humidification, confirming that recrystallization had occurred.

(Discussion)

Meltability of the saccharides used in the present experiment when heated at 140° C. was evaluated. As a result, melting was observed with the "saccharides with a low melting point," while there were no apparent changes with the "saccharides with a high melting point." Moreover, because only the endothermic peak of the "saccharides with a low melting point" disappeared with heating of physical mixtures, it appears that only the "saccharide with a low melting point" melted. That is, it appears that it is possible for only the "saccharide with a low melting point" of these mixtures to melt and make the particles of "saccharide with a high melting point" adhere. Moreover, it was made clear that when the saccharide converts to amorphous with melting, it is recrystallized by humidification. Consequently, it was clarified that improvement of stability can be realized by crystallization when a saccharide with a low melting point converts to amorphous and there is a chance that hardness will decrease, and the like, due to absorption of moisture during storage, and the like.

EXPERIMENT 2

Tests Relating to Raising Hardness of Model Tablets (Mannitol/maltose)

(Method)

Model tablet A (tablet A hereafter) was prepared as follows: First, 450 g mannitol were sifted with a sieve (20 mesh) and then granulated using a fluid bed granulator with 250 g aqueous maltose solution (20 w/w %) as the binder. Then 0.5% w/w magnesium stearate was added to this granulation product and mixed, and tablets of approximately 200 mg per 1 tablet were made using a rotary tableting machine. Tableting pressure was adjusted as needed to obtain a tablet hardness of approximately 1 kp, and it was approximately 0.1 t/punch. Tablet A was heated and/or humidified as described below (group 1: heat-treated only, group 2: humidified after heat treatment, group 3: heat-treated after humidification, and humidified once again). The treatment conditions of each process were heat treatment for 5 minutes at 140° C. using a program oven (model MOV-112P, Sanyo), and humidification treatment involved humidification for 18 hours under conditions of 25° C. and 75% RH using a thermostatic chamber at constant humidity (Tabaiespec, PR-35C) and then drying for 3 hours under conditions of 30° C. and 40% RH. Moreover, crystal form was evaluated as needed for each process by performing DSC determinations. Furthermore, tablet stability of group 1 was evaluated under conditions of 25° C. and 60% RH.

(Results)

A rise in hardness of tablet A by approximately 4-times was seen with heating only (group 1), but a reduction in hardness was observed (Table 1) in the stability evaluations (conditions of 25° C., 60% RH) that followed. When DSC determinations of tablet A after heat treatment were performed, it was confirmed that the maltose had converted to amorphous and it was felt that moisture absorption by amorphous maltose was the cause of the reduction in hardness. DSC determinations were performed on tablets that had been humidified (group 2) for the purpose of crystallization of the maltose that had converted to amorphous, but crystallization was not seen. In addition, crystallization of maltose was seen with the first humidification of group 3. The peak derived from maltose crystals disappeared after this was heat treated, confirming that melting of the maltose had occurred in this tablet as well. Furthermore, crystallization of maltose was not observed when this was humidified once again.

TABLE 1

Changes in hardness of tablets of the present invention (kp)

| | Tablet A (group 1) |
|---|---|
| Before heat treatment | 1.2 |
| After heat treatment | 5.7 |
| 1 hr after storage at 25° C. and 60% | 0.3 |
| 2 hr | 0.1 |
| 4 hr | 0.3 |
| 8 hr | 0.0 |
| 24 hr | 0.2 |
| 120 hr | 0.2 |

(Discussion)

A rise in hardness with heat treatment was observed with tablet A. It appeared that this rise in hardness apparently was due to firm adhesion of particles of "saccharide with a high melting point" as a result of the "saccharide with a low melting point" melting because the peak of the maltose crystals disappeared in the DSC determinations (group 3).

Stability under conditions of 25° C. and 60% RH was confirmed because maltose that has converted to amorphous has a low critical relative humidity and there is a chance that hardness will drop with absorption of moisture. As a result, a reduction in hardness of tablet A (group 1) was observed. An attempt was made to humidify tablets that had been heat treated in order to increase the critical relative humidity and improve stability by crystallizing the maltose (group 2). However, a peak derived from the maltose crystals was not seen and almost no crystallization occurred. As shown by Experiment 1, crystallization was seen with physical mixtures and it therefore appeared that crystallization was delayed by making the surface area of the tablet relatively small. Consequently, it is possible to present a pharmaceutical preparation with which the rise in tablet strength can be retained when maltose is used as the saccharide of the present invention by, for instance, sealing in a non-moisture permeable packaging material.

EXPERIMENT 3

Tests Relating to a Rise in Hardness of Model Tablets (Mannitol/trehalose, Mannitol/erythritol)

(Method)

Model tablets B and C were prepared as follows: First, 450 g mannitol were sifted with a sieve (20 mesh) and then granulated using a fluid bed granulator with 250 g aqueous trehalose solution (model tablet B, tablet B hereafter) or aqueous erythritol solution (model tablet C, tablet C hereafter) (20 w/w %) as the binder. Then 0.5% w/w magnesium stearate was added to this granulation product and mixed, and tablets of approximately 200 mg per 1 tablet were made using a rotary tableting machine. Tableting pressure was adjusted as needed to obtain a tablet hardness of approximately 1 kp, and it was approximately 0.1 t/punch for tablet B and approximately 0.25 t/punch for tablet C. The model tablets were heated and/or humidified as described below (group 1: heat-treated only, group 2: humidified after heat treatment, group 3: humidified). The heat treatment conditions for tablet B were 9 minutes at 140° C. and the heat treatment conditions for tablet C were 5 minutes at 140° C., and the humidification conditions were the same as in Experiment 2. Stability of hardness, the friability, and the disintegration time in the buccal cavity of these tablets when set aside at 25° C. and 60% RH was evaluated for up to 24 hours. Moreover, DSC determinations were performed and crystal form was evaluated as need for each process.

(Results)

A rise in hardness by 2.5-times~8-times was observed with heat treatment of both tablets B and C (Tables 2 and 3). When crystal form was evaluated using DSC at this time, the trehalose of tablet B was amorphous and the erythritol of tablet C was crystals. When the stability of tablet B under conditions of 25° C. and 60% RH was evaluated, a temporary reduction in hardness that was thought to be due to absorption of moisture was observed with tablet B (Table 2, group 1). However, there was almost complete recovery from this reduction in hardness in 24 hours. The fact that this was accompanied by crystallization of the trehalose was confirmed by DSC. There was almost no drop in hardness, indicating that there was stability, with group 2 that was humidified after heat treatment for the purpose of promoting crystallization. Furthermore, almost the same crystallization of group 2 was true for group 3, which was made by humidification only, which is the conventional production method. Consequently, it was made clear that it is possible to obtain a tablet of superior properties by using that heat treatment/humidification treatment of tablet B when compared to humidification treatment only. Since the erythritol of tablet C is crystals, there was almost no absorption of moisture and it was all but stable at 25° C. and 60% RH (Table 3). Consequently, humidification treatment after heating (group 2) was not performed. Erythritol is a crystalline saccharide and therefore, there was almost no rise in hardness with humidification only (Table 3, group 3).

TABLE 2

Properties of tablet of the present invention (tablet B)

| | Treatment group | | | | | | | | |
|---|---|---|---|---|---|---|---|---|---|
| | Group 1 | | | Group 2 | | | Group 3 | | |
| | Hardness (kp) | Friability (%) | vivo (s) | Hardness (kp) | Friability (%) | vivo (s) | Hardness (kp) | Friability (%) | vivo (s) |
| Before heating | 0.8 | 4.80 | 13 | 0.8 | 4.80 | 13 | 0.8 | 4.80 | 13 |
| After heating | 6.4 | 0.66 | 23 | 6.4 | 0.66 | 23 | ↓ | ↓ | ↓ |
| After humidification 25° C. 60% | ↓ | ↓ | ↓ | 5.9 | 0.88 | 28 | 3.2 | 1.58 | 17 |
| 1 hr | 5.2 | — | — | 5.7 | — | — | 3.1 | — | — |
| 2 hr | 1.6 | — | — | 5.9 | — | — | 3.1 | — | — |
| 4 hr | 1.5 | — | — | 6.2 | — | — | 3.4 | — | — |
| 8 hr | 4.9 | — | — | 6.1 | — | — | 3.1 | — | — |
| 24 hr | 5.6 | 0.92 | 20 | 5.2 | 0.90 | 27 | 2.5 | 1.57 | 20 |

TABLE 3

Properties of tablet of the present invention (tablet C)

| | Group 1 | | | Group 3 | | |
|---|---|---|---|---|---|---|
| Treatment group | Hardness (kp) | Friability (%) | vivo (s) | Hardness (kp) | Friability (%) | vivo (s) |
| Before heating | 2.1 | 1.34 | 24 | 2.1 | 1.34 | 24 |
| After heating | 5.2 | 0.81 | 30 | ↓ | ↓ | ↓ |
| After humidification 25° C. 60% | ↓ | ↓ | ↓ | 2.3 | 1.03 | 32 |
| 1 hr | 4.6 | — | — | 3.4 | — | — |
| 2 hr | 5.7 | — | — | 3.6 | — | — |
| 4 hr | 7.5 | — | — | 2.6 | — | — |
| 8 hr | 4.0 | — | — | 2.9 | — | — |
| 24 hr | 4.6 | 0.72 | 45 | 2.5 | 1.00 | 20 |

(Discussion)

Trehalose is a saccharide of high moldability that becomes amorphous. As a result of the present experiment, it was made clear that trehalose easily crystallizes under conditions of 25° C. and 60% RH and under conventional humidification and drying conditions. Moreover, once trehalose crystallized, it was stable under conditions of 25° C. and 60% RH. Consequently, trehalose is a useful saccharide in the preparation of quick-disintegrating tablets in the buccal cavity using heat treatment.

Erythritol is a crystalline saccharide of low moldability. It is a saccharide that does not function as a binder by conventional methods, but the present invention was successful in raising tablet strength as a result of melting because this saccharide has a low melting point. Since its original nature is a crystalline sugar, crystallization by humidification, and the like, is not necessary and it is also useful in improving productivity.

EXAMPLE 1

Above-mentioned Experiments 3, Tablet B, Group 1

After sifting 450 g mannitol (Towa kasei Co., Ltd.) with a sieve (20 mesh), granulation was performed using a fluid-bed granulator (Ohkawara Seisakujo) with 250 g of an aqueous trehalose (Hayashibara Co., Ltd.) solution (20 w/v %) as the binder. Then 0.5% magnesium stearate was mixed with this granulation product and tablets ((φ 8.5 mm, 10.2 mmR), tablet hardness of 0.8 kp (n=5)) of 200 mg per 1 tablet were made under a tableting pressure of approximately 0.1 t/punch using a rotary tableting machine. Next, these tablets were heated for 9 minutes at 140° C. using a program oven (model MOV-112P, Sanyo) and then set aside for 30 minutes at room temperature. Disappearance of the endothermic peak derived from trehalose crystals was confirmed at this time using DSC, proving that the trehalose was amorphous. Then these tablets were humidified at 25° C./75% RH and stored for 18 hours while moist using a thermostatic chamber at constant humidify (Tabaiespec Co., Ltd., PR-35C). Next, they were dried for 3 hours at 30° C. (humidity of 40%) to obtain the tablet of the present invention. The tablets that were obtained showed a hardness of 6.4 kp (n=5), a friability of 0.66% (100 rounds), a disintegration time in the buccal cavity of 20 seconds (n=1), and a porosity of 30.6%. Moreover, as a result of DSC determinations of the tablets that were obtained, an endothermic peak derived from trehalose crystals was seen, indicating that the trehalose had crystallized.

Comparative Example 1 (Above-mentioned Experiment 3, Tablet B, Group 3)

The tablets that were granulated and tableted as in Example 1 were humidified at 25° C./75% RH and stored for 18 hours while moist using a thermostatic chamber at constant humidity (Tabaiespec Co., Ltd., PR-35C) without being heated. They then were dried for 3 hours at 30° C. (humidity of 40%). The tablets that were obtained showed a hardness of 3.2 kp (n=5), friability of 1.53% (100 rounds), a disintegration time in the buccal cavity of 17 seconds (n=1), and a porosity of 30.6%. Based on these results, it was clarified that the tablet of the present invention has excellent properties in terms of hardness and the friability while retaining a fast disintegration time in the buccal cavity when compared to tablets made by humidification and drying only.

EXAMPLE 2

Above-mentioned Experiments 3, Tablet C, Group 1

After sifting 450 g mannitol (Towa kasei Co., Ltd.) with a sieve (20 mesh), granulation was performed using a fluid-bed granulator (Ohkawara Seisakujo) with 250 g of an aqueous erythritol (Hayashibara Co., Ltd.) solution (20 w/v %) as the binder. Then 0.5% magnesium stearate was mixed with this granulation product and tablets (($\phi$ 8.5 mm, 10.2 mmR), tablet hardness of 1.0 kp (n=5)) of 200 mg per 1 tablet were made under a tableting pressure of approximately 0.25 t/punch using a rotary tableting machine. Next, these tablets were heated for 2 minutes at 140° C. using a program oven (model MOV-112P, Sanyo) and then set aside for 30 minutes at room temperature to obtain the tablet of the present invention. The tablets that were obtained showed a hardness of 5.2 kp (n=5), a friability of 0.81% (100 rounds), a disintegration time in the buccal cavity of 30 seconds (n=1), and a porosity of 25.5%.

Comparative Example 2 (Experiment 3, Tablet C, Group 3)

The tablets that were granulated and tableted as in Example 2 were humidified at 25° C./75% RH and stored for 18 hours while moist using a thermostatic chamber at constant humidity (Tabaiespec Co., Ltd., PR-35C) without being heated. They then were dried for 3 hours at 30° C. (humidity of 40%). The tablets that were obtained showed a hardness of 2.3 kp (n=5), friability of 1.03% (100 rounds), a disintegration time in the buccal cavity of 32 seconds (n=1), and a porosity of 25.5%. Based on these results, it was clarified that the tablet of the present invention has excellent properties in terms of hardness and the friability while retaining a fast disintegration time in the buccal cavity when compared to tablets made by humidification and drying only.

EXAMPLE 3

A suspension was prepared by mixing 1,500 g famotidine, 2,000 g Aquacoat (brand name, Asahi Kasei), 150 g triacetin, and 700 g purified water. This suspension was spray dried at a spraying rate of 30 g/min, inlet temperature of 120° C., and disk rotating speed of 8,000 rpm using a spray dryer (Ohkawara Kakoki Co., Ltd., L-8) to obtain famotidine particles. Mean particle diameter at this time as 91 $\mu$m. Separately, 4,578.6 g mannitol (Towa kasei Co., Ltd.), 60 g aspartame (Ajinomoto Co., Ltd.), and 165.2 g peppermint flavor powder (T. Hasegwa Co., Ltd.) were granulated with 15% w/w aqueous solution containing 244.2 g maltose (Hayashibara Co., Ltd., brand name Sunmalt-S) in a fluid-bed granulator (Freund Industry Co., Ltd, FLO-5). After mixing 574.8 g famotidine particles that were obtained and 40 g calcium stearate with 3,385.2 g of this granulation product, 200 mg tablets containing 20 mg famotidine per 1 tablet were manufactured using a rotary tableting machine. Next, these tablets were humidified at 25° C./75% RH and stored for 24 hours while moist using a thermostatic chamber at constant humidify (Tabaiespec Co., Ltd., PR-35C). Then they were dried for 3 hours at 30° C. and 40% RH. The tablets that were obtained were heated for 2 minutes at 140° C. using a program oven (model MOV-112P, Sanyo Co., Ltd.) and set aside for 30 minutes at room temperature to obtain the tablet of the present invention. The tablets that were obtained show a hardness of 5.9 kp (n=5), friability of 0.14% (100 rounds), a disintegration time in the buccal cavity of 15 seconds (n=1), and a porosity of 25.5%.

Comparative Example 3

Tablets were obtained by granulation, tableting, and humidification and drying as in Example 3. The tablets that were obtained without heating showed a hardness of 3.7 kp (n=5), friability of 0.38% (100 rounds), a disintegration time in the buccal cavity of 15 seconds (n=1), and a porosity of 25.5%. Based on these results, it was clarified that the tablet of the present invention has excellent properties in terms of hardness and the friability while retaining a fast disintegration time in the buccal cavity when compared to tablets made by humidification and drying only.

EXAMPLE 4

After sifting 450 g mannitol (Towa kasei Co., Ltd.) with a sieve (20 mesh), granulation was performed using a fluid-bed granulator (Ohkawara Seisakujo) with 250 g of an aqueous maltose (brand name Sunmalt-S, Hayashibara Co., Ltd.) solution (20 w/v %) as the binder. Then 0.5% magnesium stearate was mixed with this granulation product and tablets (($\phi$ 8.5 mm, 10.2 mmR), tablet hardness of 1.2 kp (n=5)) of 200 mg per 1 tablet were made under a tableting pressure of approximately 0.15 t/punch using a rotary tableting machine. Next, these tablets were heated for 5 minutes at 140° C. using a program oven (model MOV-112P, Sanyo) and then set aside for 30 minutes at room temperature to obtain the tablet of the present invention. The tablets that were obtained showed a hardness of 6.9 kp (n=5), a friability of 0.39% (100 rounds), a disintegration time in the buccal cavity of 22 seconds (n=1), and a porosity of 35.6%.

EXAMPLE 5

After sifting 475 g mannitol (Towa kasei Co., Ltd.) with a sieve (20 mesh), granulation was performed using a fluid-bed granulator (Ohkawara Seisakujo) with 125 g of an aqueous maltose (brand name Sunmalt-S, Hayashibara Co., Ltd.) solution (20 w/v %) as the binder. Then 0.5% magnesium stearate was mixed with this granulation product and tablets (($\phi$ 8.5 mm, 10.2 mmR), tablet hardness of 1.0 kp (n=5)) of 200 mg per 1 tablet were made under a tableting pressure of approximately 0.1 t/punch using a rotary tableting machine. Next, these tablets were heated for 5 minutes at 140° C. using a program oven (model MOV-112P, Sanyo) and then set aside for 30 minutes at room temperature to obtain the tablet of the present invention. The tablets that were obtained showed a hardness of 7.8 kp (n=5), a friability of 0.67% (100 rounds), a disintegration time in the buccal cavity of 23 seconds (n=1), and a porosity of 33.2%.

EXAMPLE 6

After sifting 400 g mannitol (Towa kasei Co., Ltd.) with a sieve (20 mesh), granulation was performed using a fluid-bed granulator (Ohkawara Seisakujo) with 500 g of an aqueous maltose (brand name Sunmalt-S, Hayashibara Co., Ltd.) solution (20 w/v %) as the binder. Then 0.5% magnesium stearate was mixed with this granulation product and tablets ((φ 8.5 mm, 10.2 mmR), tablet hardness of 0.9 kp (n=5)) of 200 mg per 1 tablet were made under a tableting pressure of approximately 0.03 t/punch using a rotary tableting machine. Next, these tablets were heated for 5 minutes at 140° C. using a program oven (model MOV-112P, Sanyo) and then set aside for 30 minutes at room temperature to obtain the tablet of the present invention. The tablets that were obtained showed a hardness of 4.4 kp (n=5), a disintegration time in the buccal cavity of 20 seconds (n=1), and a porosity of 42.7%.

EXAMPLE 7

After sifting 490 g mannitol (Towa kasei Co., Ltd.) with a sieve (20 mesh), granulation was performed using a fluid-bed granulator (Ohkawara Seisakujo) with 67 g of an aqueous maltose (brand name Sunmalt-S, Hayashibara Co., Ltd.) solution (15 w/v %) as the binder. Then 0.5% magnesium stearate was mixed with this granulation product and tablets ((φ 8.5 mm, 10.2 mmR), tablet hardness of 0.8 kp (n=5)) of 200 mg per 1 tablet were made under a tableting pressure of approximately 0.1 t/punch using a rotary tableting machine. Next, these tablets were heated for 10 minutes at 140° C. using a program oven (model MOV-112P, Sanyo) and then set aside for 30 minutes at room temperature to obtain the tablet of the present invention. The tablets that were obtained showed a hardness of 3.9 kp (n=5), a disintegration time in the buccal cavity of 20 seconds (n=1), and a porosity of 29.3%.

EXAMPLE 8

After sifting 450 g mannitol (Towa kasei Co., Ltd.) with a sieve (20 mesh), granulation was performed using a fluid-bed granulator (Ohkawara Seisakujo) with 333 g of an aqueous erythritol (Hayashibara Co., Ltd.) and maltitol (Hayashibara Co., Ltd.) solution (7.5 w/v % each, 15 w/v % as a whole) as the binder. Then 0.5% magnesium stearate was mixed with this granulation product and tablets ((φ 8.5 mm, 10.2 mmR), tablet hardness of 0.9 kp (n=5)) of 200 mg per 1 tablet were made under a tableting pressure of approximately 0.04 t/punch using a rotary tableting machine. Next, these tablets were heated for 10 minutes at 120° C. using a program oven (model MOV-112P, Sanyo) and then set aside for 30 minutes at room temperature to obtain the tablet of the present invention. The tablets that were obtained showed a hardness of 4.8 kp (n=5), a friability of 0.3% or less (100 rounds), a disintegration time in the buccal cavity of 20 seconds (n=1), and a porosity of 32.2%.

EXAMPLE 9

After sifting 450 g lactose (Freund Industry Co., Ltd.) with a sieve (20 mesh), granulation was performed using a fluid-bed granulator (Ohkawara Seisakujo) with 250 g of an aqueous maltitol (Hayashibara Co., Ltd.) solution (20 w/v %) as the binder. Then 0.5% magnesium stearate was mixed with this granulation product and tablets ((φ 8.5 mm, 10.2 mmR), tablet hardness of 0.9 kp (n=5)) of 200 mg per 1 tablet were made under a tableting pressure of approximately 0.03 t/punch using a rotary tableting machine. Next, these tablets were heated for 2.5 minutes at 160° C. using a program oven (model MOV-112P, Sanyo) and then set aside for 30 minutes at room temperature to obtain the tablet of the present invention. The tablets that were obtained showed a hardness of 5.6 kp (n=5), a friability of 0.3% or less (100 rounds), a disintegration time in the buccal cavity of 27 seconds (n=1), and a porosity of 42.1%.

EXAMPLE 10

After sifting 900 g mannitol (Towa kasei Co., Ltd.) with a sieve (20 mesh), granulation was performed using a fluid-bed granulator (Ohkawara Seisakujo) with 400 g of an aqueous erythritol (Hayashibara Co., Ltd.) solution (20 w/v %) and 133.3 g of an aqueous maltitol (Hayashibara Co., Ltd.) solution (15 w/v %) as the binder. Then 1% sucrose fatty acid ester (Mitsubishi-Kagaku Foods) was mixed with this granulation product and tablets ((φ 8.5 mm, 9.0 mmR), tablet hardness of 0.4 kp (n=5)) of 200 mg per 1 tablet were made using a rotary tableting machine. Next, these tablets were heated under the conditions shown in Table 4 using a program oven (model MOV-112P, Sanyo) and then set aside for 30 minutes at room temperature to obtain the tablet of the present invention (porosity of 34.1%). The property values of the tablets that were obtained are also shown in Table 4.

TABLE 4

Heat treatment conditions and tablet property values in Example 10

| Treatment temperature/ time | | 5 min | 10 min | 20 min | 30 min | 60 min |
|---|---|---|---|---|---|---|
| 120° C. | Hardness (Kp) | 3.3 | 5.6 | 5.6 | 5.0 | 5.5 |
| | Friability (%) | 0.31 | 0.17 | 0.12 | 0.08 | 0.15 |
| | Disintegration time in the buccal cavity (sec) | 12 | 17 | 16 | 17 | 16 |
| 130° C. | Hardness (Kp) | 4.6 | 6.2 | 6.4 | | |
| | Friability (%) | 0.39 | 0.24 | 0.23 | | |
| | Disintegration time in the buccal cavity (sec) | 13 | 16 | 20 | | |
| 140° C. | Hardness (Kp) | 6.3 | 7.6 | | | |
| | Friability (%) | 0.15 | 0.10 | | | |
| | Disintegration time in the buccal cavity (sec) | 13 | 29 | | | |

EXAMPLE 11

After sifting 250 g acetaminophen (Yoshitomi Fine Chemicals) and 200 g mannitol (Towa kasei Co., Ltd.) with a sieve (24 mesh), granulation was performed using a fluid-bed granulator (Ohkawara Seisakujo) by spraying 200 g of an aqueous erythritol (Hayashibara Co., Ltd.) solution (20 w/v %) and 66.7 g of an aqueous maltitol (Hayashibara Co., Ltd.) solution (15 w/v %) as the binder. Then 1% sucrose fatty acid ester (Mitsubishi-Kagaku Foods) was mixed with this granulation product and tablets ((φ 8.5 mm, 9 mmR), tablet hardness of 0.4 kp (n=5)) of 200 mg per 1 tablet were made using a rotary tableting machine. Next, these tablets were heated for 10 minutes at 120° C. using a program oven (model MOV-112P, Sanyo) and then set aside for 30 minutes at room temperature to obtain the tablet of the present invention. The tablets that were obtained showed a hardness of 6.9 kp (n=5), a friability of 0.23% (100 rounds), a disintegration time in the buccal cavity of 26 seconds (n=1), and a porosity of 29.6%.

EXAMPLE 12

After sifting 250 g calcium carbonate (Nitto Funka Kogyo) and 200 g mannitol (Towa kasei Co., Ltd.) with a sieve (24 mesh), the product was introduced to a vertical mixer and 40 g water were added and mixed. After this was sifted with a sieve (16 mesh), granulation was performed using a fluid-bed granulator (Ohkawara Seisakujo) by spraying 200 g of an aqueous erythritol (Hayashibara Co., Ltd.) solution (20 w/v %) and 66.7 g of an aqueous maltitol (Hayashibara Co., Ltd.) solution (15 w/v %) as the binder. Then 1% sucrose fatty acid ester (Mitsubishi-Kagaku Foods) was mixed with this granulation product and tablets ((φ 9.5 mm, 11.4 mmR), tablet hardness of 0.4 kp (n=5)) of 400 mg per 1 tablet were made using a rotary tableting machine. Next, these tablets were heated for 10 minutes at 130° C. using a program oven (model MOV-112P, Sanyo) and then set aside for 30 minutes at room temperature to obtain the tablet of the present invention. The tablets that were obtained showed a hardness of 4.6 kp (n=5), a friability of 0.48% (100 rounds), a disintegration time in the buccal cavity of 25 seconds (n=1), and a porosity of 44.9%.

EXAMPLE 13

After sifting 450 g mannitol (Towa kasei Co., Ltd.) and 40 g erythritol (Hayashibara Co., Ltd.) with a sieve (20 mesh), granulation was performed using a fluid-bed granulator (Ohkawara Seisakujo) with 200 g of an aqueous copolyvidone (Kollidon VA64, BASF) solution (5 w/v %) as the binder. Then 0.5% magnesium stearate was mixed with this granulation product and tablets ((φ 8.5 mm, 10.2 mmR), tablet hardness of 0.6 kp (n=5)) of 200 mg per 1 tablet were made using a rotary tableting machine. Next, these tablets were heated for 10 minutes at 120° C. using a program oven (model MOV-112P, Sanyo) and then set aside for 30 minutes at room temperature to obtain the tablet of the present invention. The tablets that were obtained showed a hardness of 7.3 kp (n=5), a friability of 0.20% (100 rounds), a disintegration time in the buccal cavity of 18 seconds (n=1), and a porosity of 36.9%.

EXAMPLE 14

After sifting 475 g mannitol (Towa kasei Co., Ltd.) and 15 g erythritol (Hayashibara Co., Ltd.) with a sieve (20 mesh), granulation was performed using a fluid-bed granulator (Ohkawara Seisakujo) with 200 g of an aqueous copolyvidone (Kollidon VA64, BASF) solution (5 w/v %) as the binder. Then 0.5% magnesium stearate was mixed with this granulation product and tablets ((φ 8.5 mm, 10.2 mmR), tablet hardness of 0.7 kp (n=5)) of 200 mg per 1 tablet were made using a rotary tableting machine. Next, these tablets were heated for 10 minutes at 120° C. using a program oven (model MOV-112P, Sanyo) and then set aside for 30 minutes at room temperature to obtain the tablet of the present invention. The tablets that were obtained showed a hardness of 6.2 kp (n=5), a friability of 0.37% (100 rounds), a disintegration time in the buccal cavity of 15 seconds (n=1), and a porosity of 36.7%.

EXAMPLE 15

After sifting 350 g acetaminophen (Yoshitomi Fine Chemicals), 100 g mannitol (Towa kasei Co., Ltd.) and 40 g erythritol (Hayashibara Co., Ltd.) with a sieve (20 mesh), granulation was performed using a fluid-bed granulator (Ohkawara Seisakujo) with 200 g of an aqueous copolyvidone (Kollidon VA64, BASF) solution (5 w/v %) as the binder. Then 0.5% magnesium stearate was mixed with this granulation product and tablets ((φ 8.5 mm, 10.2 mmR), tablet hardness of 0.8 kp (n=5)) of 200 mg per 1 tablet were made using a rotary tableting machine. Next, these tablets were heated for 10 minutes at 120° C. using a program oven (model MOV-112P, Sanyo) and then set aside for 30 minutes at room temperature to obtain the tablet of the present invention. The tablets that were obtained showed a hardness of 8.3 kp (n=5), a friability of 0.36% (100 rounds), a disintegration time in the buccal cavity of 31 seconds (n=1), and a porosity of 31.0%.

Comparative Example 4

After sifting 360 g mannitol (Towa kasei Co., Ltd.) with a sieve (20 mesh), granulation was performed using a fluid-bed granulator (Ohkawara Seisakujo) with 200 g of an aqueous maltitol (Hayashibara Co., Ltd.) solution (20 w/v %) as the binder. Then 0.5% magnesium stearate was mixed with this granulation product and tablets ((φ 8.5 mm, 10.2 mmR), tablet hardness of 4.6 kp (n=5)) of 200 mg per 1 tablet were made under a tableting pressure of approximately 0.1 t/punch using a rotary tableting machine. Next, these tablets were heated for 2 minutes at 140° C. using a program oven (model MOV-112P, Sanyo) and then set aside to cool for 30 minutes at room temperature. The tablets that were obtained showed a hardness of 4.0 kp (n=5) and a porosity of 22.8%. An increase in hardness was not seen by heat treatment at the melting point of maltitol (150° C.) or lower.

Comparative Example 5

Granulation with a vertical granulator was performed using 50 g water to 800 g mannitol. After drying the granulation product, 15 g PEG6000 and 0.3 g magnesium stearate were added to 284.7 g granulation product and tablets ((φ 8.5 mm, 10.2 mmR), tablet hardness of 0.4 kp (n=5)) of 200 mg per 1 tablet were made under a tableting pressure of approximately 0.1 t/punch using a rotary tableting machine. Next, these tablets were heated for 1 hour at 70° C. using a program oven (model MOV-112P, Sanyo) and then set aside for 30 minutes at room temperature. The tablets that were obtained showed a hardness of 5.1 kp (n=5), a friability of 0.37% (100 rounds), a disintegration time in the buccal cavity of 60 seconds or longer (n=1), and a porosity of 22.8%. Based on these results, it was clarified that when tablets that have been manufactured by melting with PEG6000 serving as the binder have the same hardness as the product of the present invention, the disintegration time in the buccal cavity is greatly prolonged and they do not have the properties of a quick-disintegrating tablet.

Comparative Example 6

After sifting 490 g mannitol (Towa kasei Co., Ltd.) with a sieve (20 mesh), granulation was performed using a fluid-bed granulator (Ohkawara Seisakujo) with 200 g of an aqueous copolyvidone (Kollidon VA64, BASF) solution (5 w/v %) as the binder. Then 0.5% magnesium stearate was mixed with this granulation product and tablets ((φ 8.5 mm, 10.2 mmR), tablet hardness of 0.8 kp (n=5)) of 200 mg per 1 tablet were made using a rotary tableting machine. Next, these tablets were heated for 10 minutes at 120° C. using a program oven (model MOV-112P, Sanyo) and then set aside for 30 minutes at room temperature. The tablets that were obtained showed a hardness of 1.1 kp (n=5) and a porosity of 36.5%. A rise in hardness with heat treatment was not seen with tablets that did not contain erythritol.

Industrial Applicability

The quick-disintegrating tablet in the buccal cavity of the present invention has almost the same properties as conventional oral pharmaceutical tablets, with tablet strength being higher, the friability being kept low in particular, without prolonging disintegration time in the buccal cavity when compared to conventional quick-disintegrating tablets in the buccal cavity. Therefore, it can be used with automatic unit dosing machines. The quick-disintegrating tablet in the buccal cavity can also be used with drugs that are given in large doses. Furthermore, as with conventional oral pharmaceutical tablets, the quick-disintegrating tablet in the buccal cavity of the present invention can be taken without being disintegrated in the buccal cavity, or it can be taken together with water. In addition, the tablet of the present invention can be taken after being dissolved in water, and the like, in a cup, and the like.

The quick-disintegrating tablet in the buccal cavity of the present invention, which is produced by conventional tableting machines, and manufacturing method thereof can be used for a variety of drugs and therefore, are a very popular pharmaceutical technology.

What is claimed is:

1. A quick-disintegrating tablet in the buccal cavity (i) comprising (1) a drug, (2) lactose and/or mannitol, (3) erythritol, and (4) maltitol, wherein the tablet hardness is 3 kp or higher and the friability is 1% or less and porosity is approximately 30 to approximately 50%, or (ii) comprising (1) a drug, (2) lactose and/or mannitol, (3) erythritol, and (4) copolyvidone, wherein the tablet hardness is 3 kp or higher and the friability is 1% or less and porosity is approximately 30 to approximately 50%.

2. The quick-disintegrating tablet in the buccal cavity in claim 1, wherein the amount of erythritol is 0.5 to 25 w/w % in terms of the drug and/or the diluent.

3. The quick-disintegrating tablet in the buccal cavity in claim 1, wherein said tablet (i) comprises (1) a drug, (2) lactose and/or mannitol, (3) erythritol, and (4) maltitol, wherein the tablet hardness is 3 kp or higher and the friability is 1% or less and porosity is approximately 30 to approximately 50%.

4. The quick-disintegrating tablet in the buccal cavity in claim 3, wherein said tablet (i) comprises lactose.

5. The quick-disintegrating tablet in the buccal cavity in claim 3, wherein said tablet (i) comprises mannitol.

6. The quick-disintegrating tablet in the buccal cavity in claim 3, where tablet hardness is 4 kp or higher and the friability is 0.8% or less.

7. The quick-disintegrating tablet in the buccal cavity in claim 6, wherein the friability is 0.5% or less.

8. The quick-disintegrating tablet in the buccal cavity in claim 3, wherein the amount of drug added is at least the effective amount in terms of treatment and no more than 80 w/w % tablet weight.

9. The quick-disintegrating tablet in the buccal cavity in claim 1, wherein said tablet (ii) comprises (1) a drug, (2) lactose and/or mannitol, (3) erythritol, and (4) copolyvidone, wherein the tablet hardness is 3 kp or higher and the friability is 1% or less and porosity is approximately 30 to approximately 50%.

10. The quick-disintegrating tablet in the buccal cavity in claim 9, wherein said tablet (ii) comprises lactose.

11. The quick-disintegrating tablet in the buccal cavity in claim 9, wherein said tablet (ii) comprises mannitol.

12. The quick-disintegrating tablet in the buccal cavity in claim 9, where tablet hardness is 4 kp or higher and the friability is 0.8% or less.

13. The quick-disintegrating tablet in the buccal cavity in claim 12, wherein the friability is 0.5% or less.

14. The quick-disintegrating tablet in the buccal cavity in claim 9, wherein the amount of drug added is at least the effective amount in terms of treatment and no more than 80 w/w % tablet weight.

15. The quick-disintegrating tablet in the buccal cavity in claim 1, wherein the drug is a psychoneurotic drug.

16. The quick-disintegrating tablet in the buccal cavity in claim 15, wherein the psychoneurotic drug is a member selected from the group consisting of chlorpromazine hydrochloride, amitriptyline hydrochloride, nemonapride, haloperidol, moperone hydrochloride, perphenazine, diazepam, lorazepam, chlordiazepoxide, adinazolam, alprazolam, methylphenidate, milnacipran, paroxetine, risperidone, and sodium valproate.

17. The quick-disintegrating tablet in the buccal cavity in claim 1, wherein the drug is a central nervous system drug.

18. The quick-disintegrating tablet in the buccal cavity in claim 17, wherein the central nervous system drug is selected from the group consisting of indeloxazine, idebenone, thiapride hydrochloride, bifermerane hydrochloride, and calcium homopanthothenate.

19. The quick-disintegrating tablet in the buccal cavity in claim 1, wherein the drug is a drug for the circulatory system.

20. The quick-disintegrating tablet in the buccal cavity in claim 19, wherein the drug for the circulatory system is selected from the group consisting of isosorbide nitrate, nitroglycerin, nifedipine, barnidipine hydrochloride, nicardipine hydrochloride, dipyridamole, amrinone, indenolol hydrochloride, hydralazine hydrochloride, methyl dopa, furosemide, spironolactone, guanethidine nitrate, reserpine, amosulalol hydrochloride, lisinopril, metoprolol, pilocarpine, and tasosartan.

21. A method of manufacturing a quick-disintegrating tablet in the buccal cavity, wherein the quick-disintegrating tablet (i) comprises (1) a drug, (2) lactose and/or mannitol, (3) erythritol, and (4) maltitol, wherein the tablet hardness is 3 kp or higher and the friability is 1% or less and porosity is approximately 30 to approximately 50%, or (ii) comprises (1) a drug, (2) lactose and/or mannitol, (3) erythritol, and (4) copolyvidone, wherein the tablet hardness is 3 kp or higher and the friability is 1% or less and porosity is approximately 30 to approximately 50%:

(a) the process whereby tablet starting materials including the drug, the diluent selected from lactose and/or mannitol, the saccharide with a relatively lower melting point, which is erythritol, than said drug and said diluent, and a binder agent selected from maltitol or copolyvidone are molded under the low pressure necessary for retaining the shape of a tablet, (b) the process whereby the molded product obtained by process (a) is heated to at least the temperature at which the saccharide with a low melting point will melt, and (c) the process whereby the molded product obtained by process (b) is cooled to at least the temperature at which the molten saccharide with a low melting point solidifies.

22. The method of manufacturing a quick-disintegrating tablet in the buccal cavity of claim 21, wherein by means of process (a) the drug, lactose and/or mannitol, erythritol, and maltitol and/or copolyvidone are physically mixed to obtain the tablet starting materials.

23. The method of manufacturing a quick-disintegrating tablet in the buccal cavity of claim 21, wherein by means of process (a) erythritol and maltitol and/or copolyvidone are dissolved and/or suspended in a pharmaceutically acceptable solvent and sprayed as a binder for coating and/or granulation to obtain the tablet starting materials.

24. The method of manufacturing a quick-disintegrating tablet in the buccal cavity of claim 21, wherein by means of process (a) erythritol is mixed with the drug and lactose and/or mannitol as particles and/or powder and granulation is performed using a binder solution consisting of maltitol and/or copolyvidone to obtain the tablet starting materials.

25. The method of manufacturing a quick-disintegrating tablet in the buccal cavity in claim 21, wherein by means of process (a) the tablet starting materials are molded under a tableting pressure of 25 to 800 kg/punch.

26. The method of manufacturing a quick-disintegrating tablet in the buccal cavity of claim 21, wherein by means of process (a) heating is performed at a temperature between the melting point of erythritol and the melting point of the drug and lactose and/or mannitol.

* * * * *